United States Patent
Fontana et al.

(10) Patent No.: US 11,420,981 B2
(45) Date of Patent: Aug. 23, 2022

(54) DIASTEROSELECTIVE PROCESS FOR THE PREPARATION OF THIOL- OR DISULFIDE-CONTAINING MAYTANSINOID ESTERS AND INTERMEDIATES THEREOF

(71) Applicant: Indena S.P.A., Milan (IT)

(72) Inventors: Gabriele Fontana, Milan (IT); Ruggero Beretta, Milan (IT); Maurizio Taddei, Siena (IT); Salvatore Princiotto, Milan (IT)

(73) Assignee: Indena S.P.A., Milan (IT)

( * ) Notice: Subject to any disclaimer, the term of this patent is extended or adjusted under 35 U.S.C. 154(b) by 0 days.

(21) Appl. No.: 17/603,533

(22) PCT Filed: Apr. 9, 2020

(86) PCT No.: PCT/EP2020/060214
§ 371 (c)(1),
(2) Date: Oct. 13, 2021

(87) PCT Pub. No.: WO2020/212256
PCT Pub. Date: Oct. 22, 2020

(65) Prior Publication Data
US 2022/0119408 A1    Apr. 21, 2022

(30) Foreign Application Priority Data

Apr. 18, 2019 (EP) .................................. 19170052

(51) Int. Cl.
C07D 498/18    (2006.01)
C07D 498/12    (2006.01)

(52) U.S. Cl.
CPC .................. C07D 498/12 (2013.01)

(58) Field of Classification Search
CPC .................................................... C07D 498/18
See application file for complete search history.

(56) References Cited

U.S. PATENT DOCUMENTS 7,301,019 B2    11/2007  Widdison et al.
7,598,375 B2    10/2009  Ho et al.

FOREIGN PATENT DOCUMENTS

WO    2014052537 A1    4/2014

OTHER PUBLICATIONS

Search Report and Written Opinion of PCT/EP2020/060214 dated Jul. 24, 2020.

*Primary Examiner* — Brenda L Coleman
(74) *Attorney, Agent, or Firm* — Silvia Salvadori, P.C.; Silvia Salvadori

(57) ABSTRACT

The invention discloses a process for the preparation of maytansinoid esters of formula (I) comprising a thiol or disulphide group wherein $R^1$, $R^4$ and $R^5$ and the asterisk are as defined in the description, by reacting maytansinol with an enantiopure alpha-azido acid, followed by reduction of the azido group and reacting the obtained amino-ester with a compound of formula (IX) (IX) $R^3$—S—S—X—COOH wherein X and $R^3$ are as defined in the description, or with a reactive derivative thereof and optionally reducing the obtained disulfide-containing maytansinoid ester to give a maytansinoid ester wherein $R^1$ is a —X—SH group.

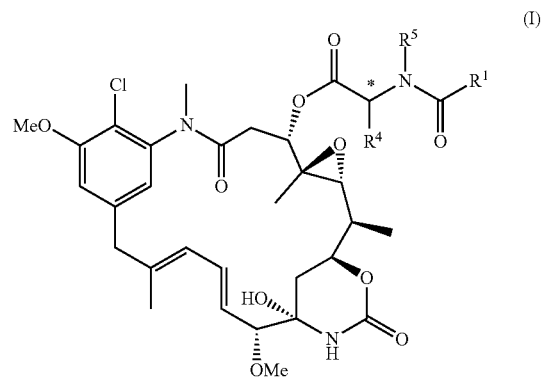

9 Claims, No Drawings

DIASTEROSELECTIVE PROCESS FOR THE PREPARATION OF THIOL- OR DISULFIDE-CONTAINING MAYTANSINOID ESTERS AND INTERMEDIATES THEREOF

This application is a U.S. national stage of PCT/EP2020/060214 filed on 9 Apr. 2020, which claims priority to and the benefit of European Application No. 19170052.5 filed on 18 Apr. 2019, the contents of which are incorporated herein by reference in their entireties.

FIELD OF THE INVENTION

The present invention relates to a diastereoselective process for the preparation of maytansinoid esters, in particular to a diastereoselective process for the preparation maytansinoid esters comprising thiol- or disulfide groups in the C-3 side chain.

BACKGROUND OF THE INVENTION

Maytansinoids are natural macrocyclic compounds (also referred to as "ansa macrolides"), endowed with cytotoxic activity. In particular, maytansinoids are antimitotic compounds and tubulin polymerization inhibitors (Ballantyne et al., Drugs 2013 73 755-765) that bind a specific site on β-tubulin (Prota et al., PNAS 2014 111 (38) 13817-13821).

The lead of these macrolides, maytansine, of formula:

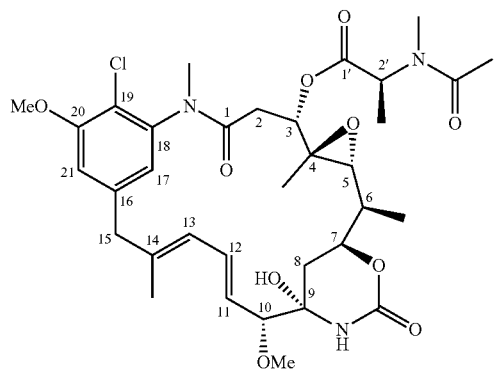 [SMILES: COc1cc2cc(c1Cl)N(C)C(=O)C[C@H](OC(=O)[C@H](C)N(C)C(C)=O)[C@]1(C)O[C@@H]1[C@@H](C)[C@@H]1C[C@@](O)(NC(=O)O1)[C@H](OC)/C=C/C=C(\C)C2]

wherein the C-3 hydroxyl group is esterified with N-acyl-N-methyl alanine, was first isolated in 1972 from the African shrub *Maytenus ovatus* (Kupchan S. M. et al, J. Am. Chem. Soc., 1972, 94 (4), pp 1354). Subsequent studies led to better isolation and characterization of maytansine and to the identification of other maytansinoids differing from maytansine in the C-3 side chain. For examples, other maytansinoids were isolated from *Maytenus buchananii* (Kupchan S. M. et al, J. Chem. Soc. Chem. Commun., 1972, (19) 1065; U.S. Pat. No. 3,896,111), *Putterlickia verrucosa* (Kupchan S. M. et al, J. Am. Chem. Soc., 1975, 97 (18), 5294), *Maytenus serrata* (Kupchan S. M. et al, J. Org. Chem. 1977 42 14 2349), *Maytenus rothiana* (Myllymaki R.W. et al, J. Nat. Prod., 1981, 44 (3), pp 340-347), *Maytenus ilicifolia* (Amhed M. S. et al., Journal of Chromatography A 1981, 213(2), 340-344), *Maytenus diversifolia* (Lee. K. H. et al, Journal of Natural Products (1982), 45(4), 509-10).

Further investigations led to the discovery that maytansinoids could also be produced by fermentative processes, mostly employing microorganisms belonging to *Nocardia* spp. (U.S. Pat. No. 4,151,042; Asai M. et al: Tetrahedron 1979 35 9 1079; Nakahama K. et al. J. Antibiot. 1981, 34 (5) 489; U.S. Pat. Nos. 4,162,940; 4,225,494; 4,320,200; 4,360,462; 4,356,265; Hatano K. et al, Agr. Biol. Chem. 1984 48 (7) 1721; U.S. Pat. Nos. 6,573,074; 6,790,954; 7,192,750).

However, the ability of maytansinoids of exerting cytotoxic activity even at nanomolar concentrations has limited their therapeutic use as anti-cancer drugs until the advent of antibody drug conjugates (ADC) complexes (Chiari R. V. J. et al, J. Med. Chem. 2006, 49, 4392).

For conjugation to antibodies, the C-3 N-acyl-N-methyl-L-alanyl ester side chain of maytansine is converted into a thiol- or disulfide-containing N-acyl-N-methyl-L-alanyl ester side chain of formula:

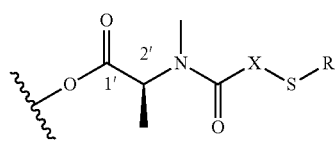

wherein X is straight or branched alkylene and R is hydrogen or —S—R', wherein R' is straight or branched lower alkyl and the wavy line indicates that the rest of the maytansine formula is unspecified. The resulting compound (herein after "thiol- or disulfide-containing maytansinoid ester") is then conjugated with an antibody.

Examples of thiol-containing maytansinoid esters are maytansinoid MD1, of formula:

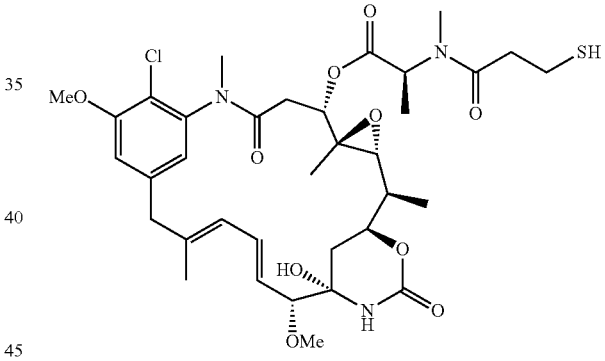

and MD4 of formula:

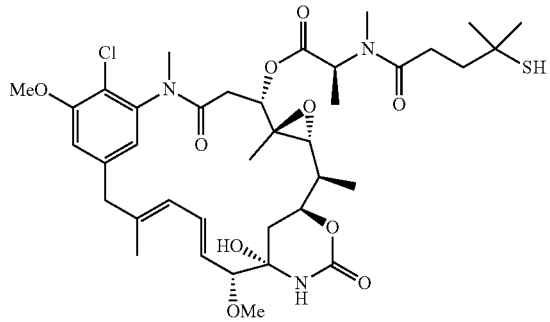 [SMILES: COc1cc2cc(c1Cl)N(C)C(=O)C[C@H](OC(=O)[C@H](C)N(C)C(=O)CCC(C)(C)S)[C@]1(C)O[C@@H]1[C@@H](C)[C@@H]1C[C@@](O)(NC(=O)O1)[C@H](OC)/C=C/C=C(\C)C2]

The first synthetic approach for the preparation of thiol- or disulfide-containing maytansinoid esters (U.S. Pat. Nos. 5,208,020, 5,416,064; 6,333,410; 7,276,497) starts from maytansinol of formula:

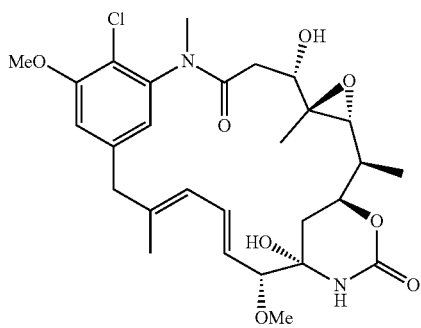 [SMILES: COc1cc2cc(c1Cl)N(C)C(=O)C[C@H](O)[C@]1(C)O[C@@H]1[C@@H](C)[C@@H]1C[C@@](O)(NC(=O)O1)[C@H](OC)/C=C/C=C(\C)C2]

which can be obtained from natural maytansinoids as disclosed, for example, in U.S. Pat. Nos. 4,151,042 and in 7,411,063.

According to this approach, maytansinol is esterified with a N-methyl-L-alanine disulfide-containing compound in the presence of an activating agent [dicyclohexylcarbodiimide (DCC)] and a Lewis acid ($ZnCl_2$); at the completion of the reaction, a corresponding disulfide-containing maytansinol ester is obtained. Conversion of the disulfide-containing maytansinoid ester into the corresponding thiol-containing maytansinoid ester can be achieved by reduction with dithiotreitol (DTT). The major drawback of this synthetic approach is the epimerization of the α-carbon of the N-methyl-L-alanine disulfide-containing compound; indeed, even if an enantiopure compound is used for the esterification reaction with maytansinol, a diastereomeric mixture of maytansinoid esters is obtained. The desired L-diastereopure maytansinoid ester can be obtained only after time consuming and expensive chromatographic separation processes, which must be carried out in high-containment environments due to the extreme toxicity of maytansinoid esters.

To overcome such problem, it has been proposed (U.S. Pat. No. 7,301,019) to react maytansinol with a disulfide-containing N-methyl-L-alanine anhydride, for example with an anhydride of formula:

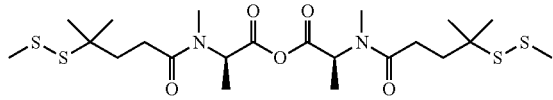

which is in turn prepared from an N-methyl-L-alanine disulfide-containing derivative of formula:

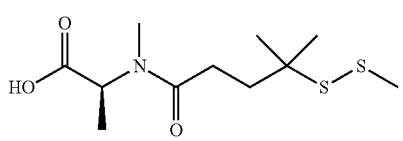 [SMILES: CSSC(C)(C)CCC(=O)N(C)[C@@H](C)C(=O)O]

This anhydride is then reacted with the maytansinol anion, generated by treatment of maytansinol with $Zn(N-SiMe_3)_2$ (zinc bis[bis(trimethylsilyl)amide]), to provide a maytansinol ester of formula:

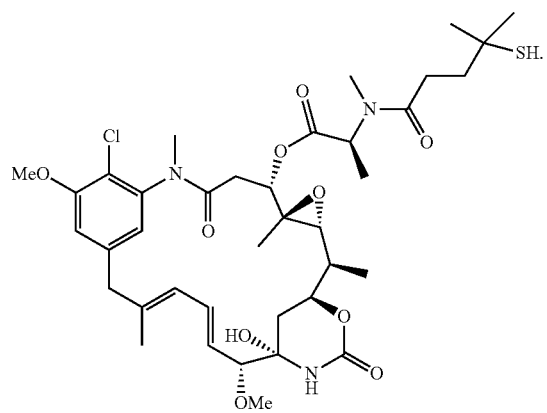 [SMILES: COc1cc2cc(c1Cl)N(C)C(=O)C[C@H](OC(=O)[C@H](C)N(C)C(=O)CCC(C)(C)S)[C@]1(C)O[C@@H]1[C@@H](C)[C@@H]1C[C@@](O)(NC(=O)O1)[C@H](OC)/C=C/C=C(\C)C2]

However, this method has the disadvantage that half of the N-methyl-L-alanine disulfide-containing derivative is wasted for the synthesis of the symmetric anhydride.

According to U.S. Pat. No. 7,301,019, a disulfide-containing amino acid is first activated as an acyl fluoride, then reacted with the maytansinol anion to provide the corresponding maytansinoid ester. Despite the enhancement of the conversion rate in favor of the desired maytansinoid ester, this method is still affected by problems related to the preparation of the acyl fluoride, such as the management of hazardous, toxic and corrosive reagents that suffer from instability and/or side reactions (Schoenebeck F. et al, Org. Lett. 2017, 19, 5740-5743).

A further method for the preparation of maytansinoid esters, which avoids complete or almost complete α-epimerization of the N-methyl-L-alanine side chain, consists in a two steps process: the first step is the acylation of maytansinol with a cyclic anhydride of formula:

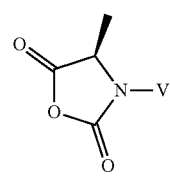

wherein V is hydrogen or straight or branched alkyl, to provide a maytansinoid alpha-amino ester of formula:

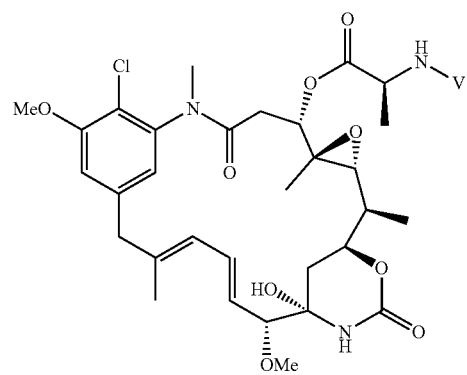

wherein V is as defined above.

The second step is the reaction of the above maytansinoid alpha-amino ester with a suitable disulfide-containing carboxylic acid in the presence of a dehydrating agent. In the first step, the rate of conversion of maytansinol is 50% in favor of the desired L-maytansinoid alpha-amino ester and 5% of undesired D-maytansinoid alpha-amino ester; the remaining 45% is unreacted starting material. In the second step, the resulting product is a 95:5 mixture in favor of the L-disulfide-containing maytansinoid ester, which is obtained as single diastereoisomer after chromatographic purification.

In a first improvement of this procedure (U.S. Pat. No. 7,598,375), the addition of a Lewis acid in the first reaction step increased the conversion of maytansinol to the corresponding L-alpha-amino maytansinoid ester up to 71%. In a second improvement (U.S. Pat. No. 9,012,629), the addition of a drying agent, such as molecular sieves, in the first step, allowed to reach a conversion rate of 80%.

Despite all improvements so far achieved, the acylation of maytansinol via the maytansinol anion remains a challenging procedure to scale up, also due to the extreme sensitivity of the anion to humidity. For this reason, the need is still felt to develop novel, robust and easily reproducible procedures for the diastereoselective preparation of maytansinoid esters, which avoid epimerization of the chiral center in the side chain and, at the same time, avoid using the maytansinol ion as reagent.

DESCRIPTION OF THE INVENTION

It has now been found that the problem of the epimerization of the chiral center in the synthesis of maytansinoid esters comprising a moiety of formula (MO-I) on the C-3 carbon atom of the maytansinoid ring:

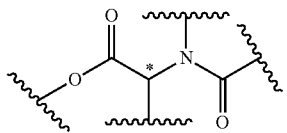

(MO-I)

wherein * represents a chiral carbon atom in the L or D configuration can be conveniently overcome by reacting maytansinol or an analogue thereof with an enantiopure alpha-azido acid, followed by reduction of the azido group. The reaction of maytansinol or analogue thereof with the alpha-azido acid provides a maytansinoid derivative (herein after referred to as "maytansinoid alpha-azido ester") bearing a moiety of formula (MO-II):

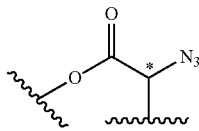

(MO-II)

on the C-3 carbon atom of the maytansinoid ring, while the reduction of the alpha azido ester provides a maytansinoid derivative (herein after "maytansinoid alpha-amino ester") bearing a moiety of formula (MO-III)

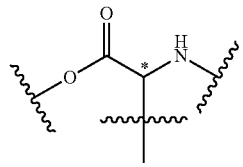

(MO-III)

on the C-3 carbon atom of the maytansinoid ring.

For the avoidance of doubt, wavy lines (or squiggy lines) denote unspecified parts of the formula of a maytansinoid compound.

Also, for the avoidance of doubt, within the present description, an "enantiopure" or "enantiomerically pure" alpha-azido acid is one in which the % enantiomeric excess (L/D or D/L, referred to the chiral carbon atom in the moiety of formula MO-II) is equal to or higher than 95%, preferably equal to or higher than 96%, more preferably equal to or higher than 97%, even more preferably equal to or higher than 98%, most preferably equal to or higher than 99%. According to a preferred embodiment, the enantiopure alpha-azido acid is one in which the L enantiomer prevails over the D enantiomer and the % enantiomeric excess is equal to or higher than 95%, preferably equal to or higher than 96%, more preferably equal to or higher than 97%, even more preferably equal to or higher than 98%, most preferably equal to or higher than 99%.

Within the present description, a maytansinol analogue is a maytansinol derivative wherein the methoxy group at positions 20 is replaced with hydroxy, alkoxy, hetero(aryloyl), aryloyl, alkanoyl, acyloxy, (hetero)aroyloxy.

In a first aspect, the present invention relates to a process for the preparation of a maytansinoid ester of formula (V):

wherein:

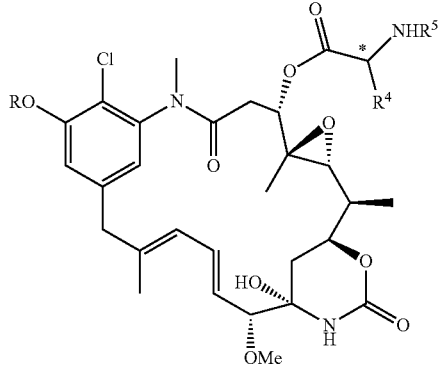

(V)

R is hydrogen or straight or branched $C_1$-$C_5$ alkyl, aryl, heteroaryl, straight or branched $C_1$-$C_5$ alkanoyl, aryloyl or heteroaryloyl;

$R^4$ is $C_1$-$C_5$ straight or branched alkyl; and $R^5$ is hydrogen or straight or branched $C_1$-$C_5$ alkyl;

and the asterisk denotes that the carbon atom is either in the L- or D configuration, preferably in the L-configuration said process comprising the following steps:
a) reacting a compound of formula (II)

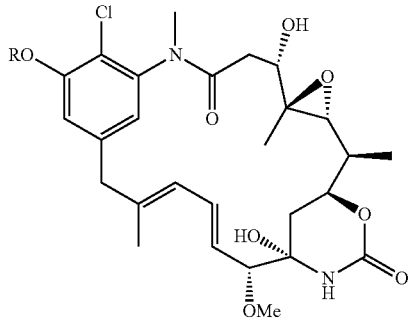
(II)

wherein R is as defined above,
with an alpha-azido acid of formula (III)

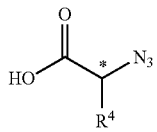
(III)

wherein $R^4$ and the asterisk are as defined above, to obtain a maytansinoid alpha-azido ester of formula (IV)

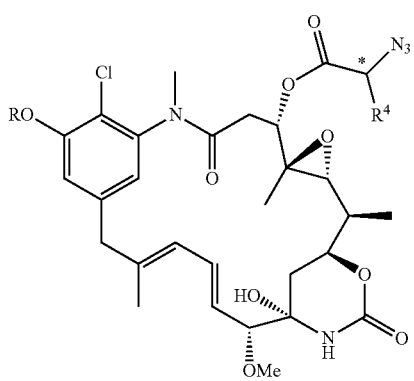
(IV)

wherein:
R, $R^4$ and the asterisk are as defined above;
b) reducing the azido group in the maytansinoid alpha-azido ester of formula (IV) to provide the maytansinoid alpha-amino ester of formula (V).

In one aspect, in formulae (III), (IV) and (V), $R^4$ is preferably methyl and in formula (V) $R^5$ is preferably $C_1$-$C_5$ alkyl, more preferably methyl.

For the avoidance of doubt, in all structural formulae reported in the present description, the asterisk denotes that the carbon atom is either in the L-or in the D-configuration, with a % enantiomeric excess (L/D or D/L) equal to or higher than 95%, preferably equal to or higher than 96%, more preferably equal to or higher than 97%, even more preferably equal to or higher than 98%, most preferably equal to or higher than 99%. According to a preferred embodiment, the carbon atom is in the L configuration, with a % enantiomeric excess equal to or higher than 95%, preferably equal to or higher than 96%, more preferably equal to or higher than 97%, even more preferably equal to or higher than 98%, most preferably equal to or higher than 99%.

In a second aspect, the present invention relates to a process for the conversion of a maytansinoid alpha amino ester (V) into a disulfide-or thiol-containing maytansinoid ester of formula (I):

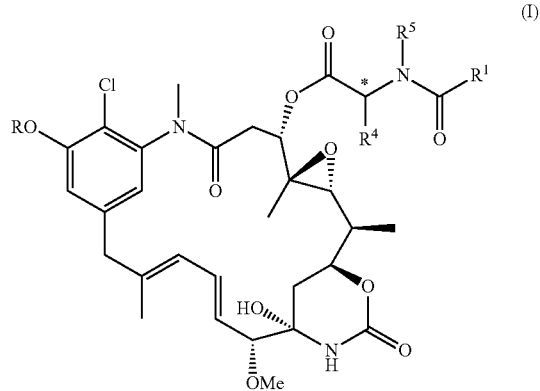
(I)

wherein:
R, $R^4$ and $R^5$ and the asterisk are as defined above; and
$R^1$ is —X—S—$R^2$ in which X is straight or branched $C_1$-$C_5$ alkylene and $R^2$ is hydrogen, straight or branched alkyl, preferably hydrogen, or —S—$R^3$ wherein $R^3$ is hydrogen or straight or branched alkyl, preferably methyl.

The maytansinoid alpha-azido ester of formula (IV) and the maytansinoid alpha-amino ester of formula (V) represent further aspects of the invention. Preferably, in the maytansinoid alpha-azido ester of formula (IV) and in the maytansinoid alpha-amino ester of formula (V) the chiral carbon atom on the C-3 side chain is in the L configuration, with a % enantiomeric purity equal to or higher than 95%, including the above-defined preferred purity ranges.

According to the present invention, the maytansinoid alpha-azido ester (IV) is obtained by reacting a compound of formula (II):

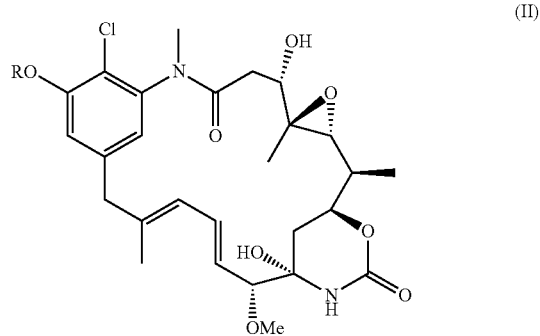
(II)

wherein R is as defined above
with an alpha-azido acid of formula (III):

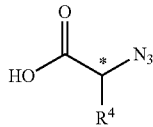

in which $R^4$ and the asterisk are as defined above in the presence of a dehydrating agent, a Lewis acid and an organic solvent. According to a preferred aspect, the compound of formula (II) is maytansinol, i.e. a compound of formula (II) in which R is methyl. According to a preferred aspect, the azide is an enantiopure azide of formula (III) in which $R^4$ is methyl, i.e. azido alanine, most preferably L-azido alanine. According to a particularly preferred aspect of the invention, maytansinol is reacted with L-azido alanine to provide a compound of formula (IV) in which R and $R^4$ are both methyl and the chiral carbon of the azido alanine residue has the L configuration. The molar ratio between the compound of formula (II) and the azide of formula (III) is typically from 1:1 to 1:10, preferably from 1:1 to 1:6; more preferably, the molar ratio is 1:4.

The Lewis acid can be selected from $ZnCl_2$, $ZnTfO_2$, $ScTfO_3$, $FeCl_3$, $InCl_3$, $InTfO_3$, $AlCl_3$, $TiCl_4$ and $CuTfO_3$; according to a preferred aspect, the Lewis acid is $ZnCl_2$.

The organic solvent is typically selected from methylene chloride ($CH_2Cl_2$), tetrahydrofuran (THF), 2-methyltetrahydrofuran (2-Me-THF), methyl acetate (AcOMe), ethyl acetate (AcOEt); according to a preferred aspect, the organic solvent is methylene chloride ($CH_2Cl_2$).

The reaction is carried out at ambient temperature and pressure. In the present application, ambient temperature means from 20° C. to 25° C. and ambient pressure means from 90 kPa to 110 kPa.

The reaction progress is typically monitored by thin layer chromatography (preferably with $CH_2Cl_2$:MeOH 9:1 as eluent). At the completion of the reaction (typically from 4 to 18 hrs), the reaction mixture is quenched, typically by addition of a suitable organic solvent, typically methylene chloride ($CH_2Cl_2$), then filtered, washed with $NaHCO_3$ and brine, and dried. The reaction crude can be subjected to purification according to methods known in the art, typically by column chromatography. In particular, a compound of formula (IV) in which both R and $R_4$ are methyl can be isolated by column chromatography on silica gel using methanol (MeOH) and methylene chloride ($CH_2Cl_2$) as eluents. However, according to a particularly convenient aspect of the invention, the maytansinoid alpha-azido ester is not subjected to purification, but it is directly converted into a maytansinoid alpha-amino ester of formula (V), as described herein below.

According to the invention, the preparation of a maytansinoid alpha-amino ester of formula (V) comprises the reduction of the azido group in the maytansinoid alpha-azido ester of formula (IV). Thus, according to the invention, a process for the manufacture of a maytansinoid alpha-amino ester of formula (V) comprises the following steps:

a) reacting a compound of formula (II) as defined above with an alpha-azido acid of formula (III) as defined above to obtain a maytansinoid alpha-azido ester of formula (IV) as defined above; and b) reducing the azido group in the maytansinoid alpha-azido ester of formula (IV) to provide a maytansinoid alpha-amino ester of formula (V).

In order to prepare a compound of formula (V) in which $R^5$ is hydrogen, step b) can be accomplished by subjecting a compound of formula (IV) to hydrogenation according to methods known in the art or by subjecting a compound of formula (V) to the Staudinger reaction. Conveniently, the alpha-azido ester of formula (IV) obtained in step a) is not purified but it is directly subjected to step b); most conveniently, steps a) and b) are carried out in one pot, i.e. the alpha-azido ester is not taken out of the reaction vessel in which step a) is carried out and the reagents for performing step b) are added to the same vessel. In greater detail, to accomplish the Staudinger reaction, the compound of formula (IV) is dissolved in a polar aprotic organic solvent, preferably tetrahydrofuran (THF), then added with triphenylphosphine ($PPh_3$) in a molar amount ranging from 1:1 to 1:5, preferably of 1:2 and water (preferably, from 7% to 8% volumes water with respect to the volume of THF) and kept under stirring at ambient temperature and pressure until completion of the reaction (typically from 24 to 48 hrs); the reaction can be monitored by thin layer chromatography, typically with $CH_2Cl_2$ and MeOH as eluents, in a $CH_2Cl_2$/MeOH volume ratio of 9:1, then the reaction mixture is evaporated under reduced pressure and purified by column chromatography on silica gel using methanol (MeOH) and methylene chloride ($CH_2Cl_2$) as eluents.

In order to prepare a compound of formula (V) is which $R^5$ is $C_1$-$C_5$ straight or branched alkyl, step b) can be accomplished by subjecting a compound of formula (IV) to the aza-Wittig reaction, in the presence of an aldehyde of formula (VI)

$$R^6CHO \qquad (VI)$$

in which $R^6$ is hydrogen or straight or branched $C_1$-$C_4$ alkyl or with a ketone of formula (VII) $R^7C(O)R^8$ in which $R^7$ and $R^8$, independently of each other, are straight or branched $C_1$-$C_4$ alkyl.

According to a preferred aspect, step b) is carried out using an aldehyde; more preferably, step b) is carried out using formaldehyde as aldehyde of formula (VI). In greater detail, the maytansinoid alpha-azido ester of formula (IV) obtained in step a) is dissolved in an organic solvent, typically selected from methylene chloride ($CH_2Cl_2$), tetrahydrofuran (THF), 2-methyltetrahydrofuran (2-Me-THF), methyl acetate (AcOMe), ethyl acetate (AcOEt), preferably methylene chloride ($CH_2Cl_2$), added with triphenylphosphine ($PPh_3$) in a molar amount ranging from 1:1 to 1:5, preferably 1:2 and left under stirring overnight at ambient temperature and pressure. Thereafter, aldehyde (VI) is added in a molar amount typically ranging from 2:1 to 10:1, preferably of 5:1 with respect to the compound of formula (IV) and the reaction mixture is left under stirring at ambient temperature and pressure until complete consumption of the compound of formula (IV) (the reaction is typically monitored by thin layer chromatography with CH2Cl2 and MeOH as eluents, in a CH2Cl2/MeOH volume ratio of 9:1). The reaction mixture is then cooled to 0° C. and added with a reducing agent, typically NaBH4, dissolved in an appropriate solvent, typically methanol (MeOH). When the reduction reaction is complete (typically in about 1-2 hrs), the reaction mixture is worked up, usually by addition of aqueous $Na_2CO_3$ and washing with water, then the resulting organic phase is dried and the resulting residue is purified according to known methods, typically by column chromatography on silica gel to provide maytansinoid alpha-amino ester (V).

Alternatively, in order to prepare a maytansinoid alpha amino ester of formula (V) in which $R^5$ is $C_1$-$C_5$ straight or branched alkyl, step b) is accomplished by reacting a maytansinoid alpha amino ester of formula (V) in which $R^5$ is hydrogen with a compound of formula (VIII):

$$R^5\text{-}L \quad\quad\quad (VIII)$$

wherein $R^5$ is as defined above and L represents a leaving group according to known methods.

Typically, a leaving group L is an alkylsulfonyl or arylsulfonyl group, preferably substituted with halogen atoms, most preferably with fluoride atoms. A preferred leaving group L, especially when $R^5$ is methyl, is the trifluromethylsulfonyl group (triflate).

As an alternative, for the manufacture of a maytansinoid alpha amino ester of formula (V) in which $R^5$ is methyl, the alkylation reaction can be carried out using any one of the following compounds: MeI, $Me_2SO_4$, $(Me_3O)BF_4$, following the procedure disclosed in Lebleu et al., Chem. Commun. 2014, 50 1836.

According to the invention, the conversion of a maytansinoid alpha-amino ester (V) into a maytansinoid ester comprising a disulfide group in the C-3 side chain can be achieved by reaction of a maytansinoid alpha-amino ester (V) with a carboxylic acid or a reactive derivative thereof comprising a disulfide moiety. In particular, the conversion into a maytansinoid ester (I) wherein $R^1$ is a —X—S—S—$R^3$ group in which X and $R^3$ are as defined above can be achieved by reaction of a compound (V) with a carboxylic acid of formula (IX);

$$R^3\text{—S—S—X—COOH} \quad\quad\quad (IX)$$

wherein X and $R^3$ are as defined above or with a reactive derivative thereof.

Preferred acids of formula (IX) include the compounds of formulae (IXa) and (IXb):

$$R^3\text{—S—S—CH}_2\text{CH}_2\text{COOH} \quad\quad\quad (IXa)$$

$$R^3\text{—S—S—(CH}_3)_2\text{CCH}_2\text{CH}_2\text{COOH} \quad\quad\quad (IXb)$$

wherein $R^3$ is as defined above
and reactive derivatives thereof.

Conveniently, in the acids of formula (IX), $R^3$ is methyl.

Thus, according to the invention, a process for the manufacture of a maytansinoid ester (I) wherein $R^1$ is a —X—S—S—$R^3$ moiety in which X and $R^3$ are as defined above comprises the following steps:

a) reacting a compound of formula (II) as defined above with an alpha-azido acid of formula (III) as defined above to obtain a maytansinoid alpha-azido ester of formula (IV) as defined above;

b) reducing the azido group in the maytansinoid alpha-azido ester of formula (IV) to provide a maytansinoid alpha-amino ester of formula (V); and c) reacting the maytansinoid alpha-amino ester of formula (V) with a carboxylic acid of formula (IX), or with a reactive derivative thereof.

Within the present description, "a reactive derivative" of a carboxylic acid of formula (IX) is a halide, preferably a fluoride or chloride, an anhydride or an urea.

Step c) is typically carried out by reacting the maytansinoid alpha-amino ester (V) with an acid of formula (IX) in a molar ratio ranging from 1:1 to 1:5, preferably in a molar ratio of 1:2 in the presence of an organic solvent, preferably selected from tetrahydrofuran (THF), 2-methyltetrahydrofuran (2-Me-THF), methyl acetate (AcOMe), ethyl acetate (AcOEt) and methylene chloride ($CH_2Cl_2$), most preferably methylene chloride ($CH_2Cl_2$) at ambient temperature and pressure and in the presence of a dehydrating agent. Conveniently, molecular sieves are employed as dehydrating agent, as they allow to carry out the reaction under mild conditions.

Upon completion of the reaction, the reaction mixture can be worked-up according to methods known in the art to isolate the desired disulfide-containing maytansinoid ester (I), which can also be submitted to purification by chromatography, for example by preparative TLC or column chromatography.

According to the invention, the conversion of a maytansinoid alpha amino ester (V) into a maytansinoid ester (I) wherein $R^1$ is a —X—SH group in which X is as defined above can be achieved by reduction of a maytansinoid ester (I) wherein $R^1$ is a —X—S—S—$R^3$ group as defined above, according to known methods.

Thus, according to the present invention, a process for the manufacture of a maytansinoid ester (I) comprising a thiol-group comprises the following steps:

a) reacting a compound of formula (II) as defined above with an alpha-azido acid of formula (III) as defined above to obtain a maytansinoid alpha-azido ester of formula (IV) as defined above;

b) reducing the azido group in the maytansinoid alpha-azido ester of formula (IV) to provide a maytansinoid alpha-amino ester of formula (V);

c) reacting the maytansinoid alpha-amino ester of formula (V) with a carboxylic acid of formula (IX) or with a reactive derivative thereof to obtain a maytansinoid ester (I) wherein $R^1$ is a —X—S—S—$R^3$ group as defined above; and d) reducing the disulfide-containing maytansinoid ester (I) to obtain a maytansinoid ester (I) wherein $R^1$ is a —X—SH group in which X is as defined above.

The following examples disclose the invention in more detail.

Experimental Section

Materials and methods

Maytansinol (II) was obtained by reduction of commercially available ansamitocin P3 (BrightGene Bio-Medical Technology Co., Ltd.), according to the procedure disclosed by Chari et al., J. Med. Chem 2006, 49, 4392.

L-Azido-alanine was prepared starting from commercially available L-alanine (Honeywell Fluka), according to the procedure disclosed by Goddard-Borger et al, Org. Lett. 2007, 9, 19, 3797.

The molecular sieves (4 Å, in pellets, 1.6 mm) were purchased from Aldrich.

NMR spectra were recorded on a Bruker 400 spectrometer, in deuterated solvents purchased from Aldrich.

HPLC analyses were performed on a VARIAN PROSTAR 325 HPLC system with a INERTSIL ODS-3V column (4.6×250 mm, 5 µm).

EXAMPLES

Example 1

Preparation of 3-O-(2'S-azidopropionyl)-maytansinol

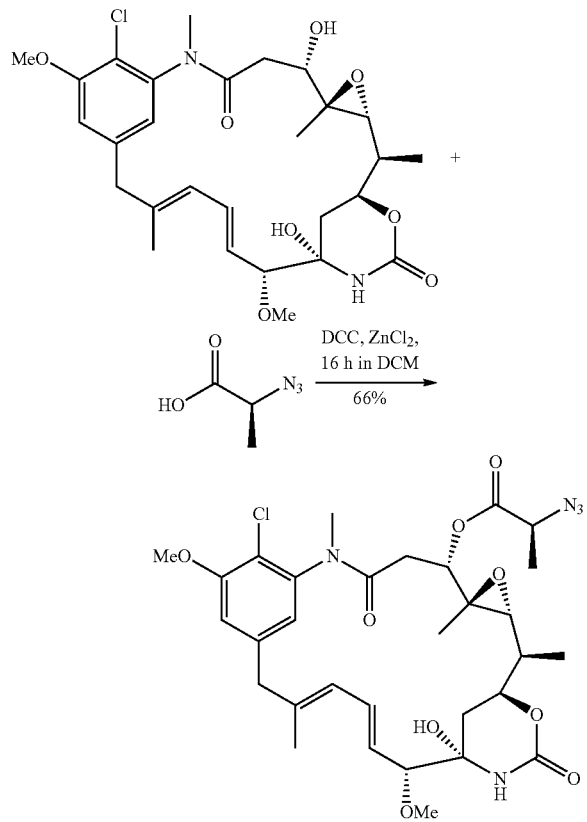

In a round bottom flask, dicyclohexylcarbodiimide DCC (2700 mg, 13 mmol) in dry dichloromethane $CH_2Cl_2$ (5 mL) and 1.9 M $ZnCl_2$ in 2-Me-THF (0.76 mL, 1.44 mmol) were added dropwise to a solution of maytansinol (680 mg, 1.20 mmol) and 2-(S)-azido propionic acid (1350 mg, 12 mmol) in dry dichloromethane (15 mL). After overnight stirring, the reaction mixture was diluted with ethyl acetate (AcOEt) and filtered. The obtained clear solution was washed with saturated $NaHCO_3$ and brine. The organic phase collected was dried over sodium sulphate $Na_2SO_4$ and the solvent was removed under vacuum. Purification of the crude product by silica gel chromatography ($MeOH:CH_2Cl_2$ 98:2) yielded 3-O-(2'S-azidopropionyl)-maytansinol as a white solid (370 mg, 0.56 mmol, Y=66%, considering the residual 15% of maytansinol).

$^1$H-NMR (400 MHz, $CDCl_3$) δ 7.10 (s, 1H), 6.82 (s, 1H), 6.42 (dd, J=15.3, 11.1 Hz, 1H), 6.33 (s, 1H), 6.19 (d, J=10.8 Hz, 1H), 5.44 (dd, J=15.3, 8.8 Hz, 1H), 5.30 (s, 1H), 4.95 (dd, J=11.9, 2.6 Hz, 1H), 4.19 (t, J=10.6 Hz, 2H), 3.96 (s, 3H), 3.94-3.81 (m, 2H), 3.50 (m, 4H), 3.34 (s, 3H), 3.16 (s, 3H), 2.82 (d, J=9.7 Hz, 1H), 2.57 (dd, J=14.0, 12.1 Hz, 1H), 2.20 (dd, J=14.1, 2.5 Hz, 1H), 1.90 (d, J=9.7 Hz, 2H), 1.77 (d, J=13.2 Hz, 3H), 1.66 (s, 5H), 1.54 (d, J=6.8 Hz, 4H), 1.25 (d, J=6.4 Hz, 3H), 0.83 (s, 3H).

HPLC analysis of the crude (C18 column, eluting with $MeCN:H_2O$ linear gradient 55% to 62% in 45 minutes), revealed the almost exclusive presence of the title compound, with a diastereoisomeric excess of 95% (97.5: 2.5 d.r.).

$R_t$=12.91 min.

Example 2

Preparation of N-methyl-L-alanine maytansinol ester

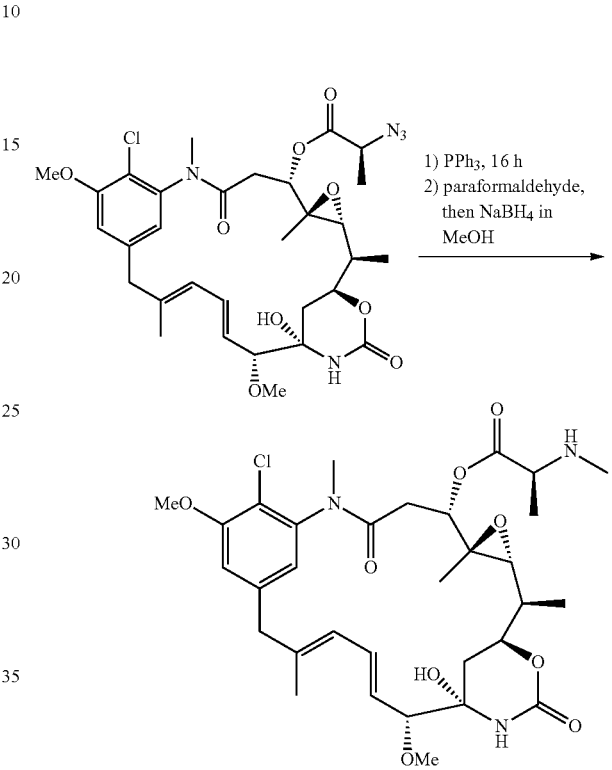

In a round bottom flask, 3-O-(2'S-azidopropionyl)-maytansinol (30 mg, 0.04 mmol) in dry dichloromethane (1 mL) was treated with triphenylphosphine $PPh_3$ (25 mg, 0.09 mmol). After overnight stirring, paraformaldehyde (7 mg, 0.23 mmol) was added and the mixture was stirred until complete conversion of the starting material (monitored by TLC), then it was cooled to 0° C. and treated with methanol (MeOH, 0.5 mL) and $NaBH_4$ (9 mg, 0.24 mmol). At the completion of the reduction, the reaction was quenched with saturated $NaHCO_3$ and diluted with dichloromethane ($CH_2Cl_2$). The organic phase was collected and washed with saturated $NaHCO_3$ and brine, dried over sodium sulfate and evaporated under reduce pressure. Purification of the crude product by silica gel chromatography (linear gradient 0-10% $MeOH:CH_2Cl_2$) afforded N-methyl-L-alanine maytansinol ester (7 mg, 0.01 mmol, Y=27%) and L-alanine maytansinol ester (17 mg, 0.03 mmol, Y=67%)

N-methyl-L-alanine maytansinol ester $^1$H NMR (400 MHz, $CDCl_3$) δ 6.87 (s, 1H), 6.83 (s, 1H), 6.43 (dd, J=15.1, 11.1 Hz, 1H), 6.25 (d, J=11.9 Hz, 1H), 6.16 (d, J=10.9 Hz, 1H), 5.49 (dd, J=15.6, 9.0 Hz, 1H), 5.00-4.91 (m, 1H), 4.24 (t, J=10.9 Hz, 1H), 3.98 (s, 3H), 3.34 (s, 3H), 3.13 (s, 3H), 2.84 (d, J=9.7 Hz, 1H), 2.63-2.51 (m, 1H), 2.40 (s, 3H), 2.23 (d, J=11.7 Hz, 1H), 1.86 (s, 3H), 1.67 (s, 3H), 1.37 (d, J=6.7 Hz, 3H), 1.28 (d, J=6.3 Hz, 3H), 0.84 (s, 3H)

L-alanine maytansinol ester $^1$H-NMR (400 MHz, CDCl$_3$) δ 6.83 (s, 1H), 6.79 (s, 1H), 6.40 (dd, J=18.4, 7.9 Hz, 2H), 6.16 (d, J=10.9 Hz, 1H), 5.52 (dd, J=15.4, 8.9 Hz, 1H), 4.92 (dd, J=11.9, 3.0 Hz, 1H), 4.28 (t, J=11.1 Hz, 1H), 3.97 (s, 3H), 3.66 (m, 1H), 3.54-3.41 (m, 4H), 3.32 (s, 3H), 3.14 (s, 3H), 2.86 (d, J=9.6 Hz, 1H), 2.57 (dd, J=14.0, 12.1 Hz, 1H), 2.21 (dd, J=14.1, 2.9 Hz, 1H), 1.65 (s, 3H), 1.46 (d, J=6.8 Hz, 3H), 1.26 (d, J=6.3 Hz, 3H), 0.83 (s, 3H).

HPLC analysis of the crude product (C18 column Inertsil™ ODS-3v, 250 mm×5 μm, MeCN:H$_2$O, linear gradient 55% to 75% in 45 minutes), revealed a R$_t$=4.34 min for the methyl amino derivative and a R$_t$=6.08 min for the corresponding primary amine.

Example 3

Staudinger reduction of 3-O-(2'S-azidopropionyl)-maytansinol

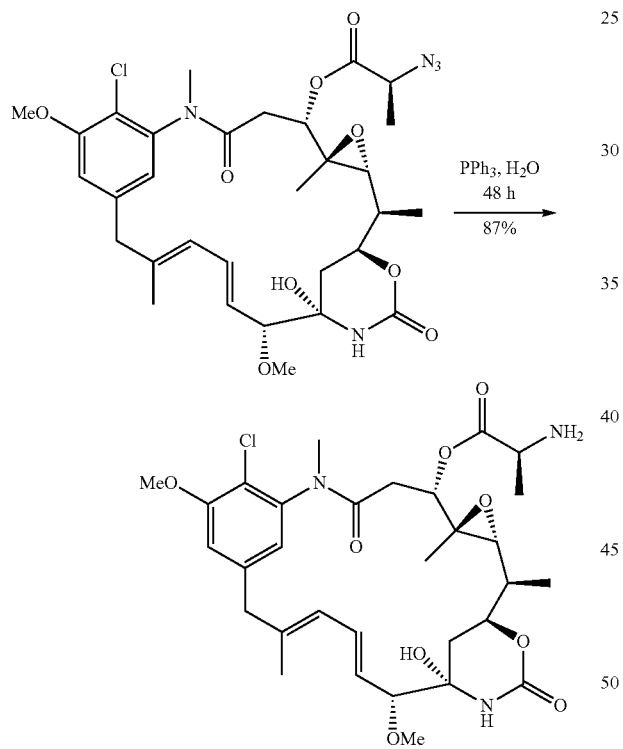

In a round bottom flask, 3-O-(2'S-azidopropionyl)-maytansinol (28 mg, 0.04 mmol) in THF (1 mL) was treated with triphenylphosphine (PPh$_3$, 20 mg, 0.08 mmol) in the presence of water (0.03 mL). The mixture was stirred for about 24-48 h, then evaporated under reduce pressure. Purification of the crude product by silica gel chromatography (1:9 MeOH:CH$_2$Cl$_2$) yielded L-alanine maytansinol ester (20 mg, 0.03 mmol, Y=87%).

$^1$H-NMR (400 MHz, CDCl$_3$) δ 6.83 (s, 1H), 6.79 (s, 1H), 6.40 (dd, J=18.4, 7.9 Hz, 2H), 6.16 (d, J=10.9 Hz, 1H), 5.52 (dd, J=15.4, 8.9 Hz, 1H), 4.92 (dd, J=11.9, 3.0 Hz, 1H), 4.28 (t, J=11.1 Hz, 1H), 3.97 (s, 3H), 3.66 (m, 1H), 3.54-3.41 (m, 4H), 3.32 (s, 3H), 3.14 (s, 3H), 2.86 (d, J=9.6 Hz, 1H), 2.57 (dd, J=14.0, 12.1 Hz, 1H), 2.21 (dd, J=14.1, 2.9 Hz, 1H), 1.65 (s, 3H), 1.46 (d, J=6.8 Hz, 3H), 1.26 (d, J=6.3 Hz, 3H), 0.83 (s, 3H).

Example 4

Preparation of N-methyl-L-alanine maytansinol ester

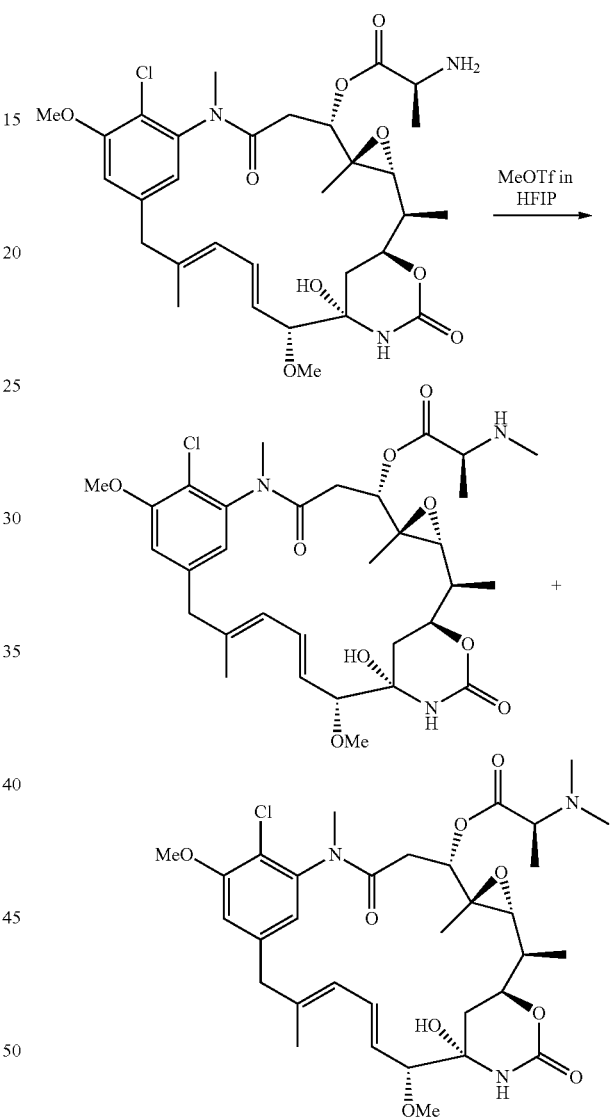

At 0° C., methyl triflate MeOTf (10 μL, 0.09 mmol) was added dropwise to a solution of L-alanine maytansinol ester (40 mg, 0.063 mmol) in 1,1,1-3,3,3-hexafluoro-2-propanol (HFIP; 1 mL). The reaction mixture was stirred for 50 minutes maintaining the temperature stable. Then, 2.0 M NH$_3$ in ethanol (60 μL, 0.13 mmol) was added to quench the reaction and the mixture was dried under vacuum. Purification of the crude product by silica gel chromatography (linear gradient 0-10% MeOH:CH$_2$Cl$_2$) provided N-methyl-L-alanine maytansinol ester (21 mg, 0.03 mmol, Y=51%). N,N-dimethyl-L-alanine maytansinol was isolated as side-product.

$^1$H NMR (400 MHz, CDCl$_3$) δ 6.87 (s, 1H), 6.83 (s, 1H), 6.43 (dd, J=15.1, 11.1 Hz, 1H), 6.25 (d, J=11.9 Hz, 1H), 6.16

(d, J=10.9 Hz, 1H), 5.49 (dd, J=15.6, 9.0 Hz, 1H), 5.00-4.91 (m, 1H), 4.24 (t, J=10.9 Hz, 1H), 3.98 (s, 3H), 3.34 (s, 3H), 3.13 (s, 3H), 2.84 (d, J=9.7 Hz, 1H), 2.63-2.51 (m, 1H), 2.40 (s, 3H), 2.23 (d, J=11.7 Hz, 1H), 1.86 (s, 3H), 1.67 (s, 3H), 1.37 (d, J=6.7 Hz, 3H), 1.28 (d, J=6.3 Hz, 3H), 0.84 (s, 3H).

Example 5

Preparation of N-methyl-L-alanine maytansinol ester (DM1-SMe)

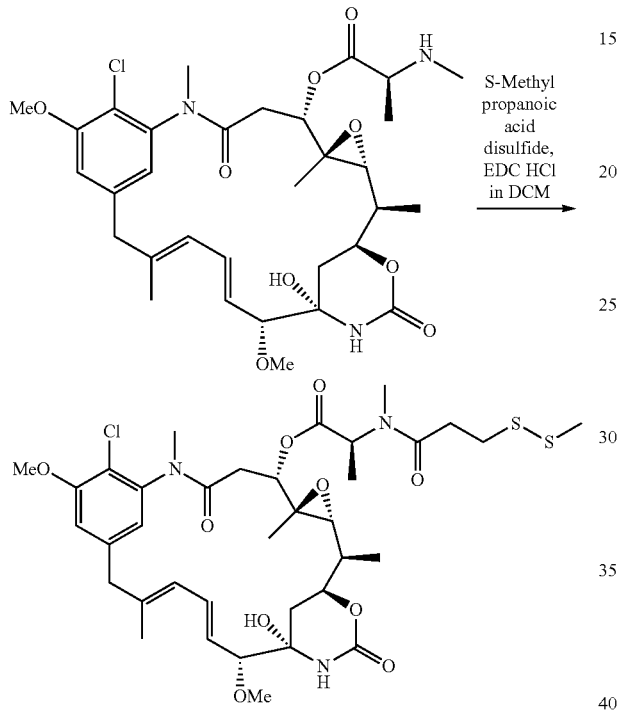

S-Methyl propanoic acid disulfide (11 mg, 0.046 mmol) was added to a solution of N-methyl-L-alanine maytansinol ester (15 mg, 0.023 mmol) in dry dichloromethane $CH_2Cl_2$ (2 ml), in the presence of molecular sieves (4 A). EDC HCl (5 mg, 0.025 mmol) was added to the mixture that was stirred overnight. At the completion of the reaction, the mixture was diluted with dichloromethane $CH_2Cl_2$ and washed with saturated $NaHCO_3$ and brine. The collected organic phase was dried over sodium sulphate $Na_2SO_4$ and evaporated under pressure. DM1-SMe was obtained without further purification.

HPLC analysis of the crude product (C18 column; $CH_3CN:H_2O$ linear gradient 55% to 80% in 30 minutes) $R_t$=13.27 min.

$^1$H-NMR (CDCl$_3$) δ 6.85 (d, J=1.5 Hz, 1H), 6.77 (d, J=11 Hz, 1H), 6.67 (d, J=1.5 Hz, 1H), 6.47 (dd, J=15, 11 Hz, 1H), 6.25 (s, 1H), 5.69 (dd, J=15, 9 Hz, 1H), 5.45 (q, J=7 Hz, 1H), 4.82 (dd, J=12, 3 Hz, 1H), 4.31 (t, J=11 Hz, 1H), 4.02 (s, 3H), 3.72 (d, J=13 Hz, 1H), 3.54 (d, J=9 Hz, 1H), 3.39 (s, 3H), 3.28 (s, 3H), 3.14 (d, J=12 Hz, 1H), 3.08 (d, J=9 Hz, 1H), 3.03-2.92 (m, 2H), 2.90 (s, 3H), 2.86-2.73 (m, 2H), 2.65 (dd, J=15, 12 Hz, 1H), 2.30 (s, 3H), 2.24 (dd, J=15, 12 Hz, 1H), 1.97 (d, J=9 Hz, 1H), 1.68 (s, 3H), 1.52-1.46 (m, 1H), 1.35 (d, J=6 Hz, 3H), 1.31 (d, J=6 Hz, 3H), 1.23-1.11 (m, 1H), 0.84 (s, 3H).

The invention claimed is:

1. A process for the manufacture of a maytansinoid ester of formula (V)

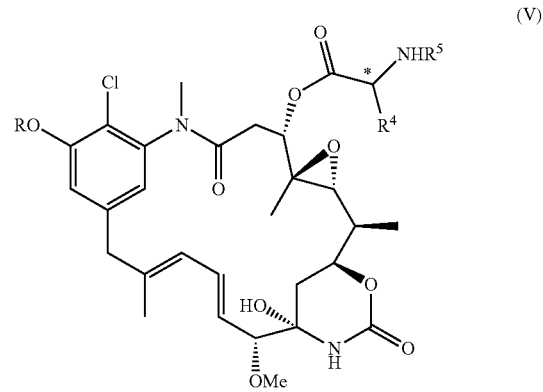

wherein:

R is hydrogen or straight or branched $C_1$-$C_5$ alkyl, aryl, heteroaryl, straight or branched $C_1$-$C_5$ alkanoyl, aryloyl or heteroaryloyl;

$R^4$ is $C_1$-$C_5$ straight or branched alkyl;

$R^5$ is hydrogen or straight or branched $C_1$-$C_5$ alkyl and the asterisk denotes that the carbon atom is either in the L- or D-configuration said process comprising the following steps:

a) reacting a compound of formula (II)

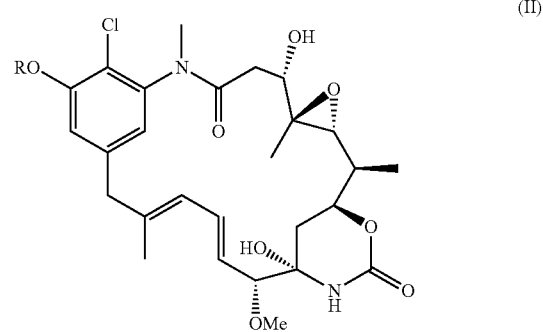

wherein R is as defined above,
with an alpha-azido acid of formula (III)

wherein R⁴ and the asterisk are as defined above,
to obtain a maytansinoid alpha-azido ester of formula (IV)

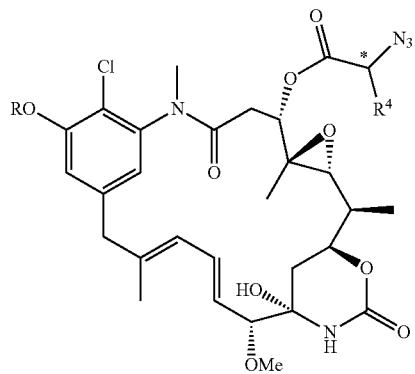

(IV)

wherein R, R⁴ and the asterisk are as defined above;
b) reducing the azido group in the maytansinoid alpha-azido ester of formula (IV) to provide the maytansinoid alpha-amino ester of formula (V).

2. A process according to claim 1 wherein R is methyl.
3. A process according to claim 1 wherein R⁴ is methyl.
4. A process according to claim 1, wherein R⁵ is methyl.
5. A process according to claim 1, wherein R⁴ is methyl and R⁵ is hydrogen.
6. A process according to claim 1, wherein step a) is performed in the presence of a dehydrating agent, a Lewis acid and an organic solvent.
7. A process for the manufacture of a maytansinoid ester of formula (I)

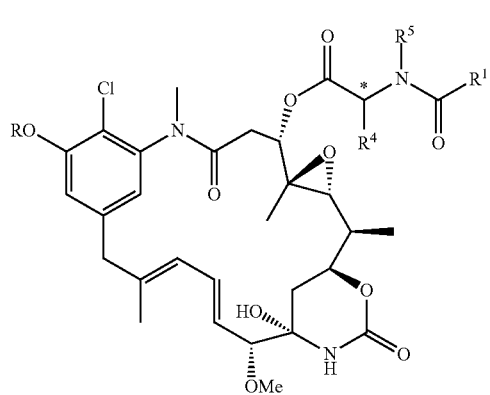

(I)

wherein
R is hydrogen or straight or branched $C_1$-$C_5$ alkyl, aryl, heteroaryl, straight or branched $C_1$-$C_5$ alkanoyl, aryloyl or heteroaryloyl;
R⁴ is $C_1$-$C_5$ straight or branched alkyl;
R⁵ is hydrogen or straight or branched $C_1$-$C_5$ alkyl;
the asterisk denotes that the carbon atom is either in the L- or D-configuration; and R¹ is —X—S—R² in which X is straight or branched $C_1$-$C_5$ alkylene and R² is hydrogen, straight or branched alkyl, or R¹ is —X—S—S—R³ wherein R³ is straight or branched alkyl;
said process comprising the reaction of a maytansinoid alpha-amino ester of formula (V), prepared according to the process of claim 1,

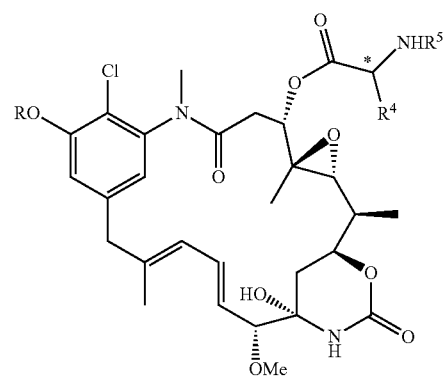

(V)

in which R, R⁴, R⁵ and the asterisk are as defined above with a carboxylic acid of formula (IX)

(IX) R³—S—S—X—COOH wherein X and R³ are as defined above,
to obtain a maytansinoid ester (I) wherein R¹ is a —X—S—S—R³ group as defined above;
and optionally reducing the disulfide-containing maytansinoid ester (I) to obtain a maytansinoid ester (I) wherein R¹ is a —X—SH group in which X is as defined above.

8. A process according to claim 7 wherein R³ is methyl.
9. A maytansinoid alpha-azido ester of formula (IV):

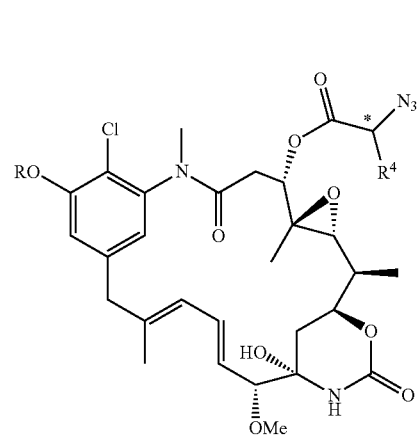

(IV)

wherein R is straight or branched $C_1$-$C_5$ alkyl, aryl, heteroaryl, straight or branched $C_1$-$C_5$ alkanoyl, aryloyl or heteroaryloyl;
R⁴ is $C_1$-$C_5$ straight or branched alkyl and the asterisk denotes that the carbon atom is either in the L- or D-configuration.

* * * * *